US00PP37673P2

(12) United States Plant Patent
Byrne et al.

(10) Patent No.: US PP37,673 P2
(45) Date of Patent: Sep. 8, 2026

(54) PEACH TREE NAMED 'TRH2B102LW'

(50) Latin Name: *Prunus persica*
Varietal Denomination: TRH2B102LW

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,385

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

U.S. PATENT DOCUMENTS

| | | | | |
|---|---|---|---|---|
| PP14,627 | P3 | 3/2004 | Byrne et al. | |
| PP14,629 | P3 | 3/2004 | Byrne et al. | |
| PP26,119 | P3 | 11/2015 | Byrne et al. | |
| 2016/0205832 | P1 * | 7/2016 | Byrne | Plt./195 |

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
Byrne and Anderson, 2013. White Delight peach series: Four medium-chill, subacid, white-fleshed peaches. HortScience 48(8):1056-1058.
U.S. Appl. No. 19/295,148, filed Aug. 8, 2025, Byrne et al.

* cited by examiner

*Primary Examiner* — Karen M Redden
(74) *Attorney, Agent, or Firm* — Dentons US LLP

(57) ABSTRACT

Disclosed is a new variety of *Prunus persica* named 'TRH2B102LW'. This new variety, which requires approximately 500 chilling units of dormancy, is considered to be a peach tree of early season maturity, which produces white-fleshed, subacid fruit that are firm with a 60-80% dark red blush with a light-yellow ground color, and suitable for the fresh fruit market.

5 Drawing Sheets

Latin name of the genus and species of the plant claimed: *Prunus persica.*

Variety denomination: 'TRH2B102LW'.

CROSS-REFERENCE TO RELATED APPLICATIONS

Peach trees developed under the same breeding program as 'TRH2B102LW' include the co-pending applications listed below.

| U.S. application Ser. No. | Title |
|---|---|
| U.S. 19/295,148 | PEACH TREE NAMED 'TRH2E122W' |
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,370 | PEACH TREE NAMED 'TX2B449LW' |
| U.S. 19/336,372 | PEACH TREE NAMED 'TX2C465CW' |

-continued

| U.S. application Ser. No. | Title |
|---|---|
| U.S. 19/336,375 | PEACH TREE NAMED 'TRH1C104LW' |
| U.S. 19/336,377 | PEACH TREE NAMED 'TRH3C111' |
| U.S. 19/336,380 | PEACH TREE NAMED 'TRH2C108W' |
| U.S. 19/336,383 | PEACH TREE NAMED 'TRH2E116L' |
| U.S. 19/336,368 | PEACH TREE NAMED TRH3E88LW' |

BACKGROUND OF THE INVENTION

This invention relates to a peach tree and, more specifically, to a peach tree referred to as a variety of *Prunus persica* named 'TRH2B102LW', which requires approximately 500 chilling units of dormancy, produces a firm, clingstone, white-fleshed, subacid peach with a 60-80% dark red blush over a light-yellow ground color that matures early in the season. The present peach tree was the result of an ongoing Stone Fruit Breeding Program in College Station, Brazos County, Texas. To this end, controlled crosses were made each year to produce seedling populations from which improved progenies are evaluated and selected.

'TRH2B102LW' was derived from a population created by crossing the medium chill, white-fleshed, subacid peach 'White Delight Two' (not patented) with pollen of the low-chill, yellow-fleshed, peach 'TexFirst' (patented). The seed from the 'White Delight Two' x 'TexFirst' hybrid family were planted in 2011 in an experimental plot in Floresville, TX. 'TRH2B102LW' was marked for subsequent observation in 2013 and noted as having exceptional characteristics.

'TRH2B102LW' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-203), Somerville (2016-2023) and Fairfield (2016-2020), Texas. This evaluation clearly demonstrated that the re-propagated trees were true to the characteristics of the original seedling in all observable aspects.

SUMMARY OF THE INVENTION

The 'TRH2B102LW' peach is characterized by producing clingstone, white-fleshed, subacid fruit that ripens early in the season and produces a firm, fruit with a 60-80% dark red blush over a light-yellow ground color. In this regard, the present variety of peach tree bears fruit that are ripe for commercial harvesting and shipment in mid-May, when the fruit is grown in the medium chill zone of Texas. 'TRH2B102LW' blooms about one week before its female parent 'White Delight Two' (not patented; U.S. Ser. No. 14/544,507, abandoned), and about 3 weeks after its pollen parent 'TexFirst' (patented, U.S. Plant Pat. No. 26,199). It ripens about 2 weeks before its female parent and about 3 weeks after its pollen parent. 'TRH2B102LW' differs from its white-fleshed, subacid, peach female parent as it ripens about 2 weeks before and requires ~100 less chilling hours to fruit. 'TRH2B102LW' also differs from 'White Delight Two' as it has showy flowers whereas 'White Delight Two' has non showy flowers. It differs from its low chill, early ripening, yellow-fleshed peach pollen parent as it is a medium-chill, white-fleshed and subacid peach.

'TRH2B102LW' differs from other selections 'TRH2E122W' (U.S. Ser. No. 19/295,148), 'TRH2C108W' (U.S. Ser. No. 19/336,380) and 'TRH3C114W' (U.S. Ser. No. 19/336,169) derived from the same parents as they have acid flesh flavor as compared to the subacid flesh flavor of the 'TRH2B102LW'. In addition, 'TRH2E122W' differs from 'TRH2B102LW' as it has more anthocyanin accumulation in the flesh (70-80% vs. 20%), has globose leaf glands rather than reniform leaf glands, has non showy flowers rather than showy flowers, and ripens 3 weeks later than does 'TRH2B102LW'. All three related varieties bloom about 2 weeks before 'TRH2B102LW'. Although 'TRH2C108W' ripens with 'TRH2B102LW', 'TRH3C114W' ripens about one week later than 'TRH2B102LW' 'TRH2B102LW' has showy flower and reniform leaf glands whereas the two commercial, medium-chill, subacid, white-fleshed peaches 'White Delight One' (not patented; U.S. Ser. No. 14/544,514, abandoned) and 'White Delight Two' have non showy flowers and globose leaf glands. In addition, 'White Delight One' ripens about two weeks before and 'White Delight Two' ripens about two weeks later than 'TRH2B102LW'. This new subacid, white-fleshed, clingstone, early ripening peach exhibits potential to be commercialized in regions that have chilling requirements that are moderately low.

BRIEF DESCRIPTION OF THE DRAWINGS

This new variety of peach tree is illustrated by the accompanying photographs of plants in their 5th year of growth as grown in Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
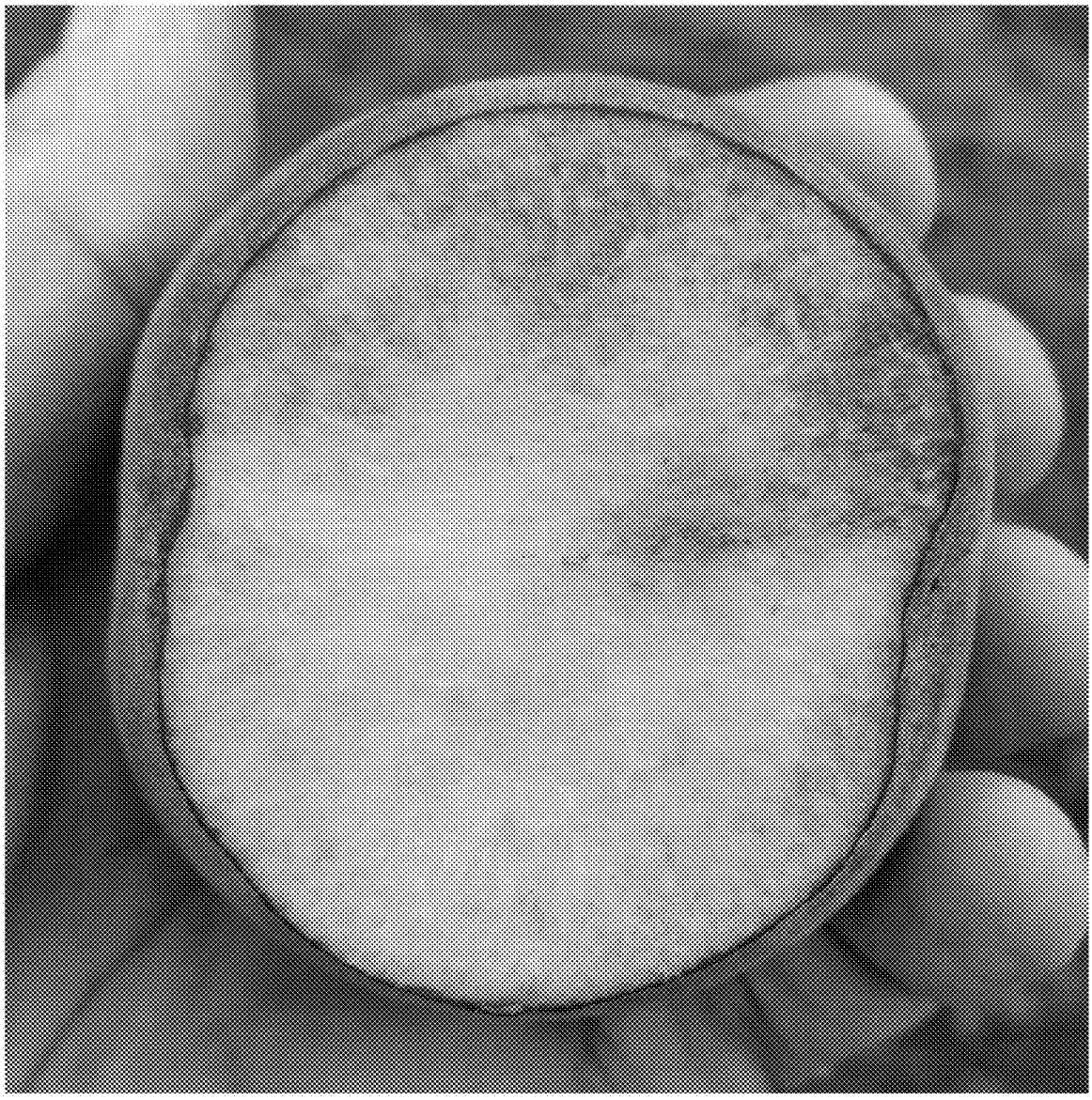
FIG. 1. Fruit of 'TRH2B102LW' produced in Pleasanton, Texas showing internal coloration.
Figure 2:
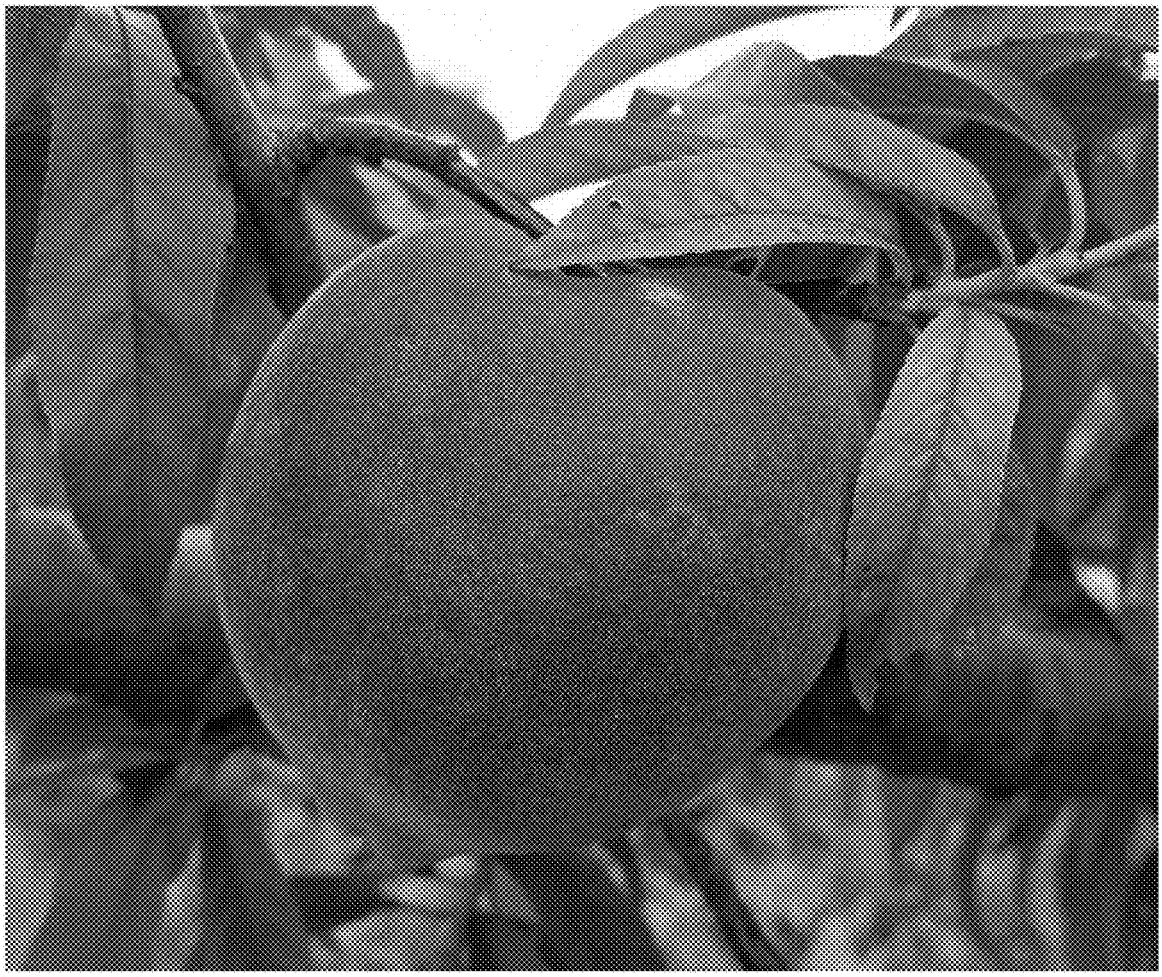
FIG. 2. 'TRH2B102LW' fruit produced in Pleasanton, Texas showing shape and external coloration.
Figure 3:
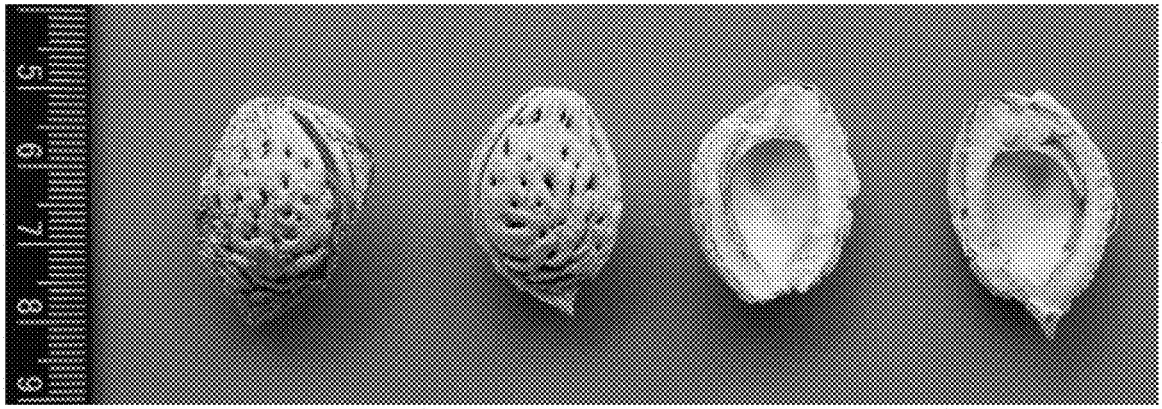
FIG. 3. Photograph of the endocarps of 'TRH2B102LW' peach. The ruler is in centimeters.
Figure 4:
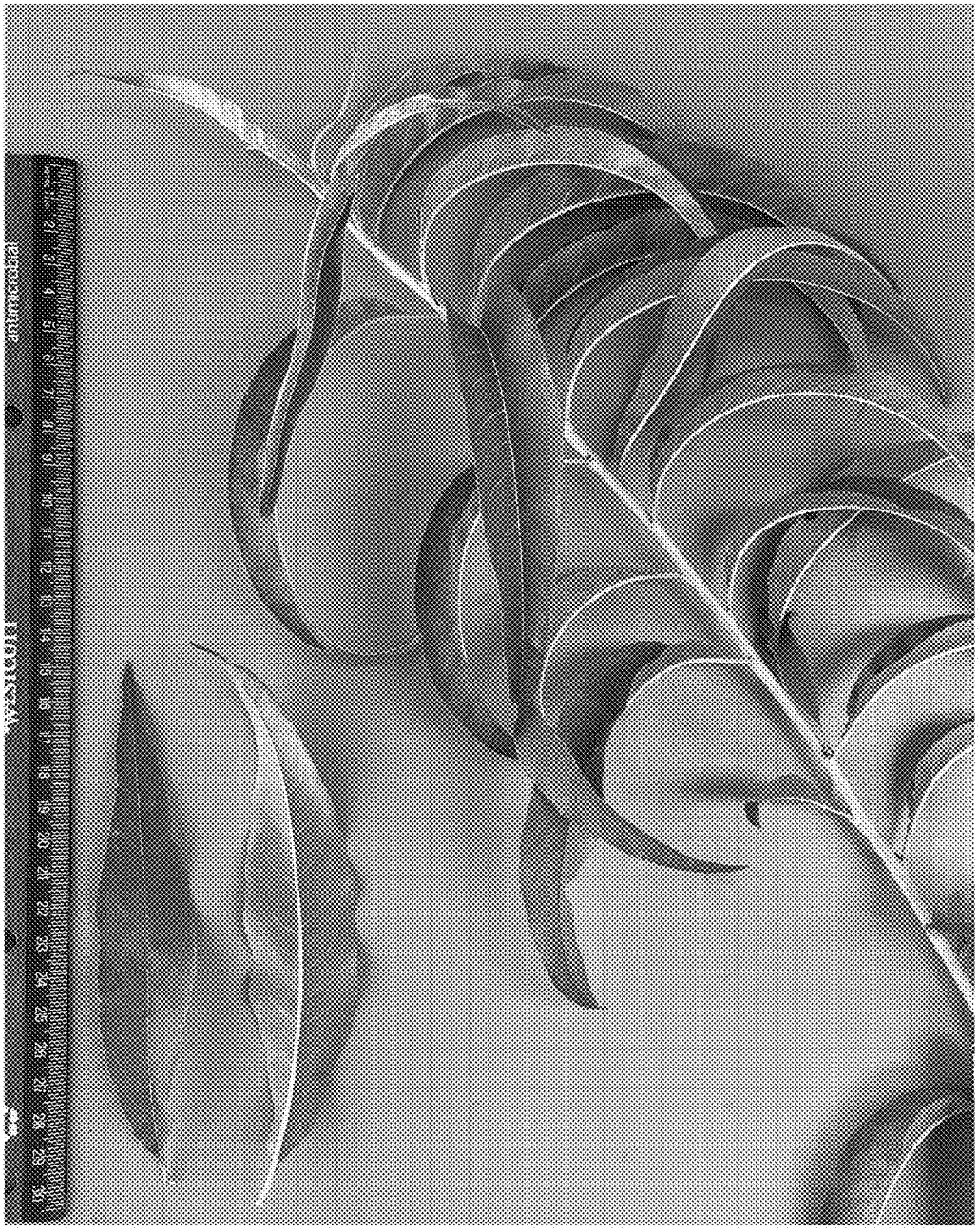
FIG. 4. A stem showing the leaves of 'TRH2B102LW' peach. The ruler is in centimeters FIG. 5. A stem showing the flowers of 'TRH2B102LW' peach. The ruler is in centimeters.
Figure 5:
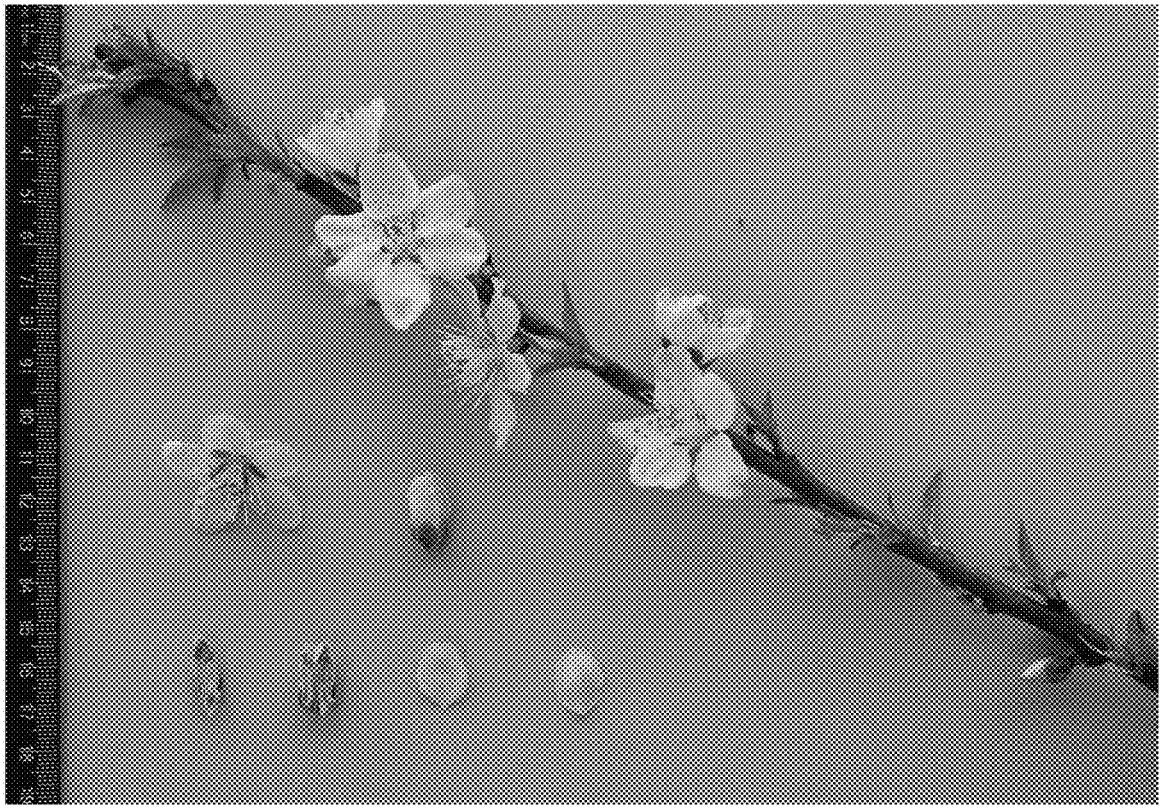

Referring more specifically to the pomological details of this new and distinct variety of peach tree, the following has been observed under the ecological conditions prevailing at the experimental orchards in the medium chill zone of Texas (Fairfield, Pleasanton, and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars ripening in the medium chill zone of Texas.

*Height*.—8-9 feet (2.4-2.7 m) at the end of the 2024 growing season.

*Width*.—7 feet width (2.1 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH2B102LW' peach has been trained to an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 1 to 2.5 feet (0.3-0.8 m). Vigor is medium to medium low compared to other common peach varieties grown in the medium chill zone of Texas.

*Regularity of bearing*.—Regular absent temperatures of 28° F. or less during bloom and considered hardy in the medium chill zone of Texas.

Trunk:

*Size*.—Approximately 3 inches (7.6 cm) in diameter and 10.25 inches (26 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS2001) present are 156C and 156D of the Greyed-White Group, 178A of the Greyed-Red Group, 187A of the Greyed-Purple Group, 195C, 195D, 196A, 196B, 196C and 196D of the Greyed-Green Group and N200D of the Brown Group.

Branches:

*Thickness*.—About 4.3 cm in diameter as measured 10 cm from the trunk on a three-year old tree.

*Surface texture*.—Average and appearing furrowed on wood that is several years old.

*Lenticels*.—Numerous flat, oval lenticels present. The lenticels range in size from approximately 4 to 6 mm in width and were approximately 1.5 to 3 mm in height.

*Current season shoots*.—Surface texture — Substantially glabrous.

*Internode length*.—Approximately 19 to 22 mm as measured in the middle of a current season stem.

*Color of mature branches*.—The predominant colors (RHS2001) are 156D of the Greyed-White Group, 166A, 176A and 177A of the Greyed-Orange Group, 178A and 178B of the Greyed-Red Group, 183 of the Greyed-Purple Group, 196D, 197D and 198D of the Greyed-Green Group and 201D of the Grey Group.

*Current season shoots*.—Color (RHS2001) — Light to medium green, 144A, 144B, N144 C, N144D, 146C and 146D of Yellow-Green Group with some reddish-brown coloration appearing on exposed surface of the shoots 59A and 59B of the Red-Purple Group, 166A of the Greyed-Orange Group, N186C and 187B of the Greyed-Purple Group and 200B and 200C of the Brown Group.

Leaves:

*Size*.—Considered small to moderately small for the species. Leaf measurements have been taken from vigorous upright current season growth approximately at mid-shoot.

*Leaf length*.—Approximately 90 to 95 mm.

*Leaf width*.—Approximately 23 to 26 mm.

*Leaf thickness*.—Less than 1 mm.

*Leaf form*.—Lanceolate.

*Leaf tip form*.—Acuminate.

*Leaf upper surface color* (*RHS*2001).—Green, approximately 137B and 137C of the Green Group.

*Leaf lower surface color* (*RHS*2001).—Green, approximately 138A and 138B of the Green Group.

*Leaf lower mid-vein color* (*RHS*2001).—Light green, approximately 145D of the Yellow-Green Group.

*Leaf margins*.—Form — Considered crenate. Uniformity — Considered generally uniform.

*Leaf petioles*.—Length — Approximately 9 to 10 mm. Thickness — Approximately 1 to 2 mm. Texture — Glabrous. Color (RHS2001) — Light green, approximately 146D of the Yellow-Green Group.

*Leaf glands*.—Size — Approximately 4 mm in height and 1 mm in width. Number — Generally 1 per leaf. Type — Reniform. Color (RHS2001) — Brown, approximately 199A of the Grey-Brown Group.

*Leaf stipules*.—Length — Approximately 7 to 8 mm. Form — Lanceolate. Color — Green (144B, N144C, N144D, 145A and 146D of the Yellow-Green Group). The stipules are early deciduous. Ratio of wood (leaf) buds to flowering buds — Generally 2 flower buds per vegetative bud.

Flowers:

*Floral buds*.—General — The floral buds are conic in form, and slightly appressed relative to the bearing shoot. Color — Mature buds are brown, (approximately 165A and 166A of the Greyed-Orange Group and 200C and 200D of the Brown Group Mature Bud Length — Approximately 3 to 4 mm. Mature Bud Width — Approximately 1 to 2 mm.

*Blooming type*.—Mean date of full bloom in the medium chill zone of Texas was in mid-to late February (February 25$^{th}$ at Somerville and February 18$^{th}$ at Fairfield experimental plot), a 3-7 days after the commercial cultivars 'Texking' and 'Flordaking' (Andrews, 1979).

*Flower type*.—Showy.

*Flower size*.—Flower diameter at full bloom is approximately 30 to 44 mm.

*Bloom quantity*.—Considered abundant.

*Flower bud frequency*.—Normally 1 to 2 per node.

*Petal size*.—General — Considered medium to medium large for the species. Width — Approximately 12 mm. Length — Approximately 15 to 18 mm.

*Petal form*.—Broadly ovate.

*Petal count*.—Nearly always 5 to 6.

*Petal abaxial/adaxial color* (*RHS*2001).—Medium pink when young, 65B, 65C, 65D, 69A, 69B and 73D of the Red-Purple Group becoming darker near the petal claw.

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally — The petal apices appear slightly rounded.

*Flower pedicel*.—Length — Average length of 1.5 mm. Thickness — Approximately 1 mm. Color (RHS2001) — A light green, 144C, 144D, N144D, 145A and 145B of the Yellow-Green Group.

*Floral nectaries*.—Color (RHS2001) — Medium to dark orange, 24A, 24B, 25A, 25B, 25C, N25A, N25B, N25C, 28A and 28B of the Orange Group.

*Sepals*.—Surface Texture — The surface has a short, fine, wooly texture. Size — Average Length 5.2 mm; Width 5.2 mm. Form — Ovate. Sepal Count — Five sepals per flower. Color (RHS2001) — Maroon and green with a white fuzzy texture. 58A, 59C, 60A and 60B of the Red-Purple Group, 144C, 144D, N144C, N144D, 145A and 145B of the Yellow-Green Group, 155A, 155B, 155C, 155D of the White Group, 178A and 178B of the Greyed-Red Group and 183B, 183C, 184A, 184B, 185A, 185B and 187C of the Greyed-Purple Group.

*Floral cup* (*hypanthium*).—Surface Texture — Generally glabrous. Color (RHS2001) — Maroon with green, 58A, 59C, 60A and 60B of the Red-Purple Group, 144C, 144D, N144C, N144D, 145A and 145B of the Yellow-Green Group, 178A and 178B of the Greyed-Red Group and 183B, 183C, 184A, 184B, 185A, 185B and 187C of the Greyed-Purple Group.

*Anthers*.—Color (RHS2001) — Medium to dark orange. Approximately N30A, 33A and 34A of the Orange-Red Group.

*Pollen production*.—Pollen is abundant and is a dark yellow color. Approximately (RHS2001) 13A and 13BB of the Yellow Group and 14A, 14B, 15A, 15B, 15C and 16A of the Yellow-Orange Group.

*Filaments*.—Size — Variable in length, approximately 11 to 16 mm, with the filaments slightly shorter or equal in height to the pistil and below the petal height. Color (RHS2001) — White, approximately 155A and 155B of the White Group and darkening with advanced maturity.

*Pistil*.—General — Equal to slightly taller than the anther height and below the petal height. Length — Approximately 15 to 16 mm, including the ovary. Color (RHS2001) — Considered a light yellow-green when young (approximately RHS2001 1A, 1B, 1C, and 1D of the White Group) and becoming slightly darker with advancing senescence.

*Surface texture*.—The variety has a long/short, silver white pubescent pistil (approximately RHS2001 155A, 155B, 155C, and 155D of the White Group.

Fruit:

*Maturity when described*.—The present variety of fruit is described, as it would be found in its firm ripe condition at full commercial maturity. Under the ecological conditions prevailing in the medium chill zone of Texas it would be ripe in mid-May. The average ripe date at Pleasanton, Somerville and Fairfield experimental plots were May 15$^{th}$, May 19$^{th}$ and May 18$^{th}$ respectively.

*Size*.—General — Medium to medium large for the season and considered uniform. Average Cheek Diameter — Approximately 54 to 58 mm. Average Suture Diameter — Approximately 57 to 60 mm. Average Axial Diameter — Approximately 55 to 60 mm.

*Fruit form*.—Generally considered truncate with unequal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Dark pink to maroon. 39A, 47B, 53B and 53C of the Red Group, 60A of the Red-Purple Group and 183A, 183B, 184A, 185A, 187B and 187C of the Greyed-Purple Group.

*Ventral surface*.—Form — Considered uniform.

*Stem cavity*.—Width — Approximately 14 to 16 mm. Length — Approximately 21 to 24 mm. Depth — Approximately 11 to 12 mm.

*Fruit base*.—Flat.

*Fruit apex*.—Round and tapering.

*Fruit stem*.—Length — 7 to 8 mm. Thickness — 2 to 3 mm. Color (RHS2001) — Light green, varies from 139D of the Green Group to 144B, 144C, N144C, N144D and 145A of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Cracking not observed. Skin Color — Generally-Variable, with approximately 60-80% of the fruit surface covered with a medium to dark red blush. The over color is marbled to solid in its pattern. Blush Color (RHS2001) — Medium to dark red, 45A, 46A, 47A, 53A and 53B of the Red Group and 185A, 185B and 187C of the Greyed-Purple Group. Skin Ground Color (RHS2001) — Light yellow green. 1C and ID of the Green-Yellow Group and 2D, 4C, 4D, 5D and 10D of the Yellow Group.

*Flesh color* (*RHS*2001).—White, 155A, 155B, 155C and 155D of the White Group. Anthocyanin coloration of the flesh is generally medium to strong next to the skin, weak to medium centrally and weak next to the pit.

*Flesh fibers*.—Present throughout the flesh.

*Stone cavity color* (*RHS*2001).—White, 155A, 155B, 155C and 155D of the White Group.

*Flesh texture*.—Generally, the flesh is considered firm at commercial maturity.

*Ripening*.—Generally the fruit of the present variety ripens evenly.

*Flavor*.—Considered very sweet (average Brix 13.1) with a rich subacid flavor.

Stone:

*Attachment*.—Clingstone at commercial maturity.

*Stone size*.—Length — Approximately 29 to 31 mm. Width — Approximately 19 to 21 mm. Thickness — Approximately 14 to 17 mm.

*Fibers*.—Generally a few medium length fibers are attached along the entire surface of the stone.

*Stone form*.—Elliptical.

*Stone base angle*.—The stone is narrow to medium.

*Apex shape*.—Narrow to medium.

*Stone shape*.—Considered elongated.

*Stone surface*.—Surface Texture — Consists of single pits and rosettes of pits. Ridges — Numerous fine ridges are present basally and converge towards the base of the stone.

*Ventral edge*.—Medium to large.

*Dorsal edge*.—Shape-Grooved and having moderately rough edges.

*Stone color* (*RHS*2001).—The color of the dry stone is light brown, 158A of the Yellow-White Group and 159A and 159B of the Orange-White Group. The color of the inside surface of the endocarp is light brown, primarily 158A, 158B, 158C of the Yellow-White Group, 159A and 159B of the Orange-White Group and 164D and 165D of the Greyed-Orange Group.

*Tendency to split*.—Splitting not observed.

*Kernel*.—The kernel fills the endocarp at harvest and measures approximately 3 mm in thickness, 7 mm in width, and 13 mm in length. Fresh kernel is a medium brown, (RHS2001) 163A, 164B and 165B of the Greyed-Orange Group. When dried the shriveled kernels measure approximately 1 mm in thickness, 7 mm in width, and 12 to 13 mm in length. The colors of the shriveled kernels are primarily medium brown, 164A, 164B, 165B, 165C and N167A of the Greyed-Orange Group.

*Use*.—The subject variety, 'TRH2B102LW', is considered to be a medium chill peach tree of early-season maturity, which produces subacid, white-fleshed fruit which are firm with a 60-80% dark red blush over a light-yellow ground color, and which are useful for the fresh fruit market.

*Keeping quality*.—Average. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed:

1. A new and distinct variety of peach tree named 'TRH2B102LW', as illustrated and described herein.

* * * * *